United States Patent [19]
Reddersen et al.

[11] Patent Number: 5,296,689
[45] Date of Patent: Mar. 22, 1994

[54] AIMING BEAM SYSTEM FOR OPTICAL DATA READING DEVICE

[75] Inventors: Brad R. Reddersen; Thomas L. Durant, both of Eugene, Oreg.

[73] Assignee: Spectra-Physics Scanning Systems, Inc., Eugene, Oreg.

[21] Appl. No.: 843,473

[22] Filed: Feb. 28, 1992

[51] Int. Cl.$^5$ .............................................. H01S 3/10
[52] U.S. Cl. ........................................ 235/467; 359/17; 359/205; 359/212
[58] Field of Search ................ 235/467, 462; 359/15, 359/17, 19, 205, 212, 216, 566, 569

[56] References Cited

U.S. PATENT DOCUMENTS

| | | | |
|---|---|---|---|
| 3,892,488 | 7/1975 | Edmonds | 356/153 |
| 4,224,509 | 9/1980 | Cheng | 235/467 |
| 4,243,294 | 1/1981 | Noguchi | 359/205 |
| 4,309,998 | 1/1982 | Aron nee Rosa et al. | 128/303.1 |
| 4,603,262 | 7/1986 | Eastman et al. | 250/566 |
| 4,728,789 | 3/1988 | Broockman et al. | 235/457 |
| 4,758,058 | 7/1988 | Cato et al. | 235/457 |
| 4,760,248 | 7/1988 | Swartz et al. | 235/472 |
| 4,794,237 | 12/1988 | Ferrante | 235/467 |
| 4,800,256 | 1/1989 | Broockman et al. | 235/467 |
| 4,832,426 | 5/1989 | Käser | 359/19 |
| 4,841,129 | 6/1989 | Tawara et al. | 235/472 |
| 4,861,973 | 8/1989 | Hellekson et al. | 235/467 |
| 4,967,074 | 10/1990 | von Stein | 235/467 |
| 5,080,456 | 1/1992 | Katz et al. | 235/462 |
| 5,146,463 | 9/1992 | Rando | 235/467 |
| 5,177,343 | 1/1993 | Takenaka | 235/467 |

FOREIGN PATENT DOCUMENTS

0116896  8/1984  European Pat. Off. .............. 359/19

*Primary Examiner*—Davis L. Willis
*Assistant Examiner*—Yu S. Lin
*Attorney, Agent, or Firm*—Lyon & Lyon

[57] ABSTRACT

An optical scanning system including an aiming system which is particularly suitable for handheld scanners where the outgoing light is scanned over a desired angle in a scan plane. The aiming system includes a light source generating an optical beam along an outgoing optical path toward an object to be scanned; a detector for detecting light reflected off the object; an oscillating scan mirror in the outgoing optical path directing light toward the object along a scan plane; and a diffractive optical module positioned in the outgoing optical path adjacent the scan mirror, the diffractive optical module having a pair of diffractive optical elements separated by an aperture, the diffractive optical elements positioned on either side of an aperture along the scan plane, each diffractive optical element de-scanning the portion of the optical beam passing therethrough to form an aiming light beam.

21 Claims, 6 Drawing Sheets

AIMING BEAM SYSTEM FOR OPTICAL DATA READING DEVICE

BACKGROUND OF THE INVENTION

The field of the present invention relates to optical scanning systems and particularly to an aiming system for use with an optical scanning system. The invention is especially suitable for use in a laser scanner for reading bar codes such as those found on consumer products, most frequently the UPC bar code. The invention is particularly suitable for handheld scanners.

Bar code scanners, as any optical system, require an outgoing scan beam to be properly drawn over the intended target such as the bar code. A problem arises where laser scanners, in particular handheld scanners, are used to scan bar code labels located a great distance from the laser scanner. Over distances of several feet, scan lines become so diffuse that they are not readily visible on a target, making it difficult for the operator to properly aim the scanner at the target or effectively manipulate the target to be read. This difficulty arises because the path of the beam across the surface carrying the bar code label may not be readily visible to the operator of the scanner due to the high speed of movement of the beam tracing the scan line or due to low intensity of the visible scan line. Thus, for example, it has been found that targeting and reading a bar code 3 inches by 1 inch in size at a distance of five feet becomes problematic.

In response to this problem, laser scanners have been developed having a two-position trigger which causes the laser scanner to generate either a scan line or a fixed pointer beam for aiming the laser scanner. For example U.S. Pat. No. 4,760,248 discloses a portable laser diode scanner equipped with a trigger-actuated aiming light for visually locating and tracking the symbol. The pointer beam or aiming light is visible over a greater distance, because the light energy is concentrated in a spot. However, trigger-actuated aiming lights and two-position scanners have the disadvantage of requiring manual switching of the scanner between operating modes and, once switched from the pointing mode back to the scanning mode, they again leave the operator "blind" to the direction in which the scanner is pointed while scanning.

Accordingly, improved performance and targeting capability are desired to satisfy the continuing need for high performance scanners for use in a wide range of applications.

SUMMARY OF THE INVENTION

The present invention relates to an optical scanning system and particularly to an aiming system for use with an optical scanning system. The invention is particularly suitable for handheld scanners where the outgoing light is scanned over a desired angle in a scan plane. In the preferred embodiment, the aiming system includes a light source generating an optical beam along an outgoing optical path toward an object to be scanned; a detector for detecting light reflected off the object; an oscillating scan mirror in the outgoing optical path directing light toward the object along a scan plane; and a diffractive optical module positioned in the outgoing optical path adjacent the scan mirror, the diffractive optical module having a pair of diffractive optical elements separated by an aperture, the diffractive optical elements positioned on either side of an aperture along the scan plane, each diffractive optical element de-scanning the portion of the optical beam passing therethrough to form an aiming light beam.

DESCRIPTION OF THE PREFERRED EMBODIMENT

The preferred embodiments will now be described with reference to the drawings To facilitate description, any numeral identifying an element in one figure will represent the same element in any other figure.

Figure 1:
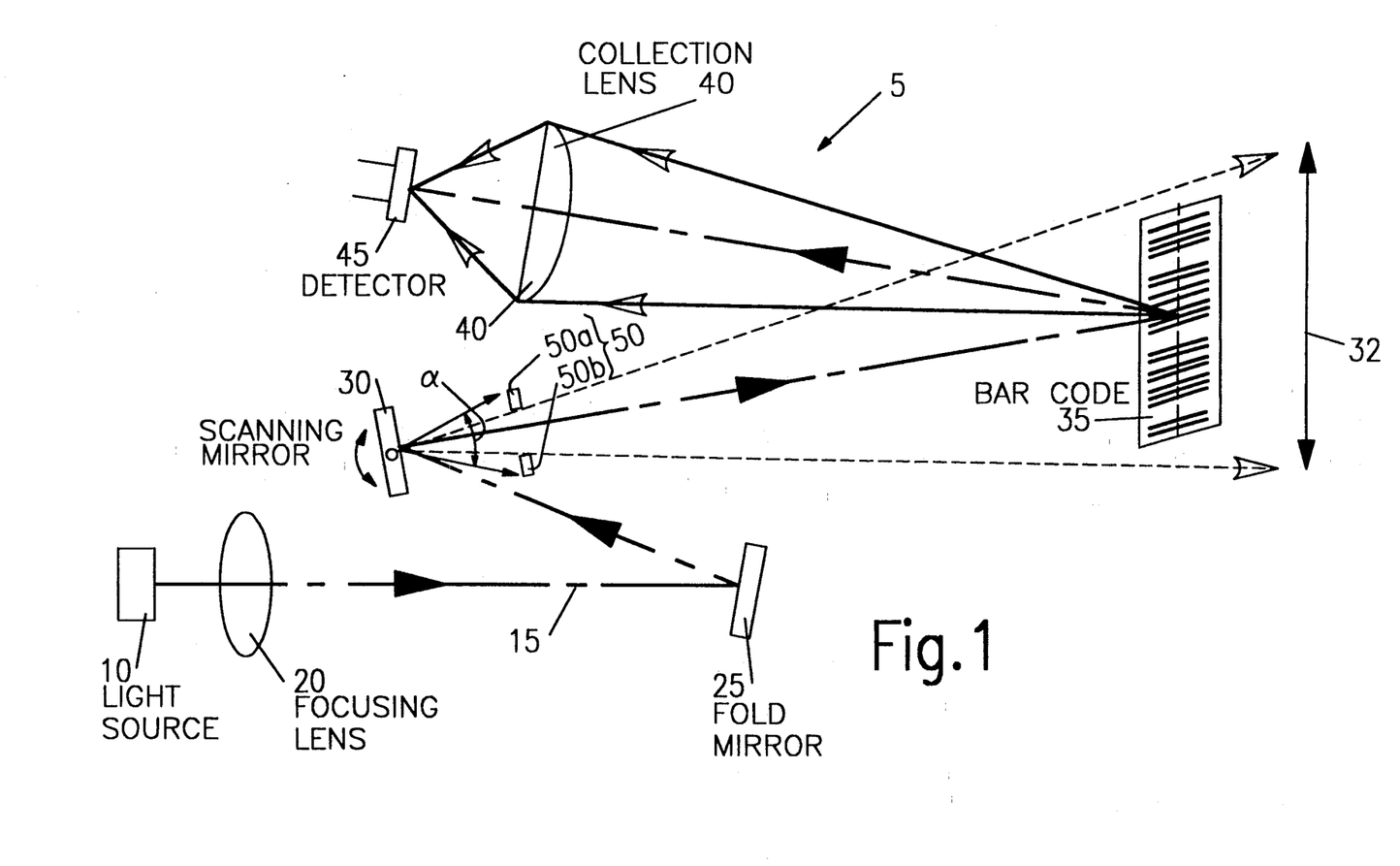
FIG. 1 is a schematic diagram illustrating a scanning system used by the present invention.

FIG. 1 is a schematic diagram of a scanning system 5 such as that which may be employed by the present invention. A light source illustrated as a laser diode 10 emits light 15 being aimed at the desired target shown in this example as a UPC bar code 35. A target may be any object desired to be read including the scanning of bar codes, industrial symbols, alphanumeric characters, and other indicia for object recognition. Light 15 from the laser diode 10 is focused by a focusing lens 20. The focused beam 15 is then reflected off fold mirror 25 and is directed to the scanning mirror 30. As the scanning mirror 30 scans (i.e. pivots, oscillates or rotates about its axis), the beam scans (in a scan plane) over a scanning beam angle $\alpha$ toward the target bar code 35. The system is designed with a scanning beam angle $\alpha$ which is greater than that required for the scan. A diffractive optical module 50 is interposed in the outgoing scanning beam path adjacent the scanning mirror 30. The diffractive optical module 50, which is described in greater detail below, is comprised of first and second diffraction or diffractive optical elements 50a and 50b separated by an aperture or window. The portion of the scan beam which does not impinge on the diffractive optical elements 50a and 50b passes through the aperture over a scan range 32. Light reflected off the bar code 35 is focused by a collection lens 40 and detected by the photodetector 45.

The portion of the optical beam impinging on the diffractive optical elements 50a and 50b are "de-scanned" or "straightened out" so that instead of exiting the scanner at a progressively expanding scanning cone of light, the beam exits as beams propagating generally parallel with the scanning system optical axis. Because the actual distance the scanning beam travels on the grating is small, the "de-scanned" beams will appear on the target as stationary bright spots along a dim scan line.

Figure 2:
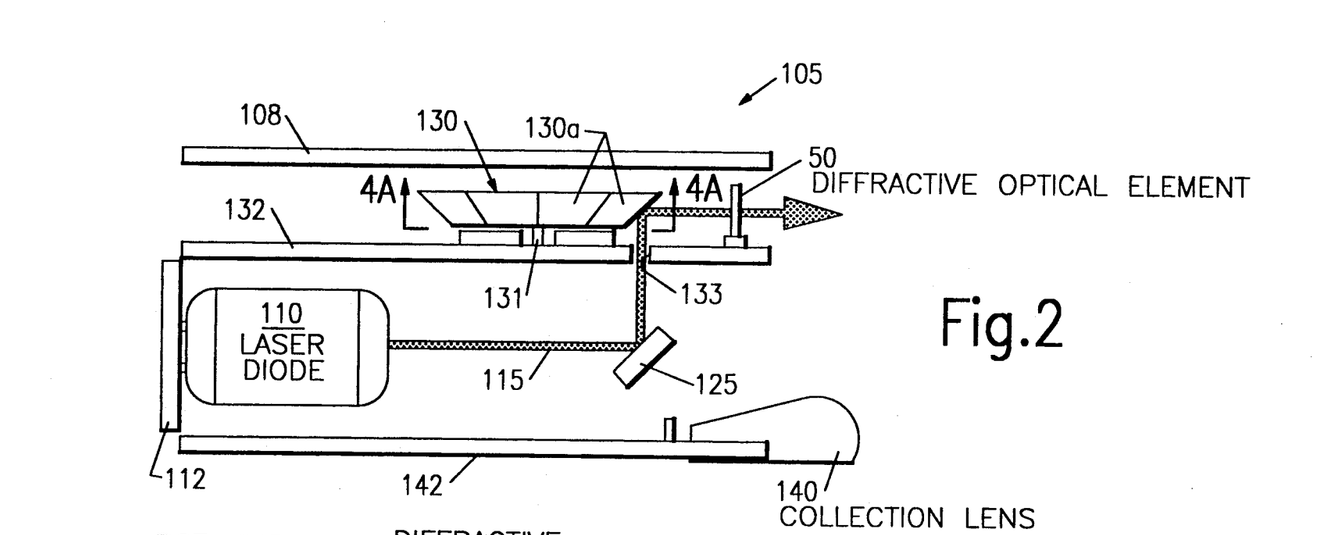
FIG. 2 is a diagrammatic side elevation view of a preferred embodiment polygon mirror scanning system having aiming optics according to the present invention.
Figure 3:
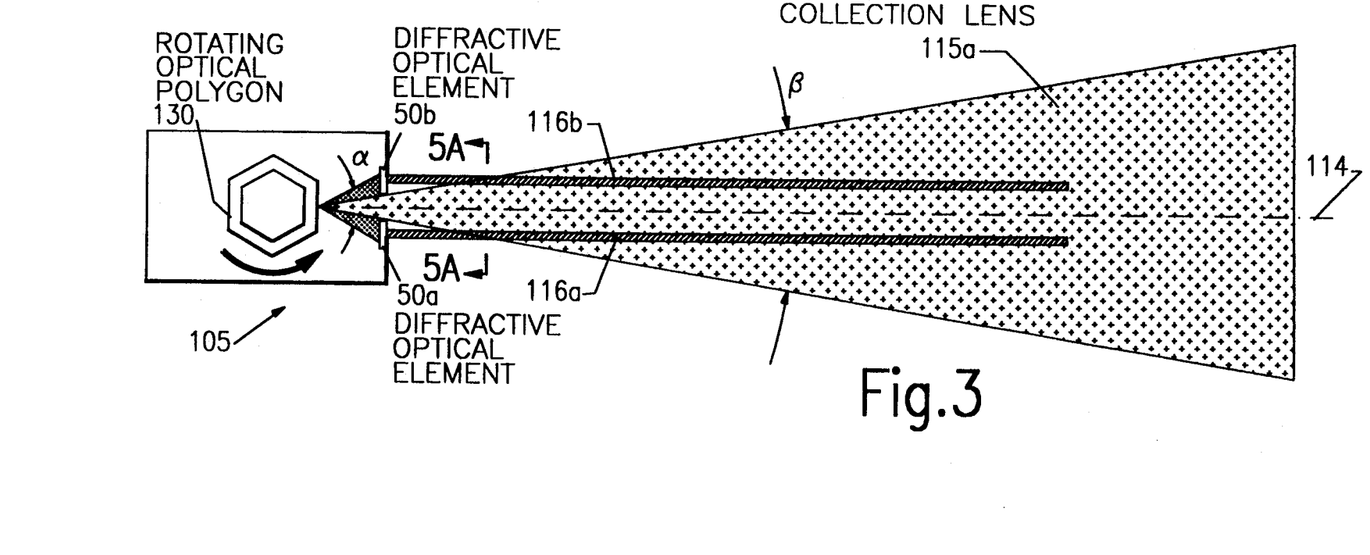
FIG. 3 is a diagrammatic top plan view of the scanning system of FIG. 2.

The preferred embodiment for the scanning system of the present invention is illustrated in FIGS. 2-3 showing a scanning system 105 employing an optical polygon 130 as the scan mirror element. A light source shown as laser diode module 110 controlled by a diode driver printed circuit board 112 generates an optical beam 115 which is focused and directed to fold mirror 125. The beam 115 is reflected off fold mirror 125 and passes through an aperture 133 in motor printed circuit board 132 onto the polygon mirror 130. A scanning beam is then directed through the module 50 and toward the target. The optical polygon 130 is rotated or pivoted about its axis 131 by a motor controlled by printed circuit board 132. Light reflecting or refracting off the target is then detected by a detector illustrated in this embodiment by a toroidal collection lens module 140.

As the polygon mirror 130 rotates, the beam scans (in a scan plane) over a scanning beam angle $\alpha$ toward the target bar code 35. As in the previous embodiment, the scanning beam angle $\alpha$ is greater than that required for the scan. The diffractive optical module 50 is interposed in the outgoing scanning beam path adjacent the scanning mirror 30. The module 50 is comprised of first and second diffractive optical elements 50a and 50b separated by an aperture or window. The portion of the scan beam which does not impinge on the diffractive optical elements 50a and 50b passes through the aperture over a scan angle $\beta$.

The portions of the optical beam on either end of the scan impinge on the diffractive optical elements 50a and 50b and are "de-scanned" or "straightened out" so that instead of exiting the scanner at a progressively expanding scanning cone of light, the beam portion exits as aiming beams 116a and 116b propagating generally parallel with the scanning system optical axis 114. The diffractive optical elements 50a and 50b are designed to "de-scan" the incoming beam 115 so that the aiming beams 116a and 116b will appear on the target as stationary bright spots along a dim scan line. In other words, light exiting the elements 50a and 50b travel as columns 116a and 116b toward the target passing through the scanning cone of light 115a. Preferably, the aiming beams impact the target (which is at approximately the expected distance from the scanner) producing aiming spots spaced in the scan plan at about the width of, for example, the bar code. By providing two separate aiming beams 116a and 116b, the user can not only determine that the scanner is correctly aimed on the target but also correctly oriented. When the aiming spots appear on each side of the bar code, the user will know the scanner has the correct orientation of the scan plane. Simply put, the scanner will scan "between the spots."

In the preferred embodiment, it is anticipated that the present invention be employed in a scanning system which may employ a variety of scanning beam generation configurations and a variety of collection configurations. Some of these systems are described in the co-pending U.S. Pat. application of James L. Durant et al. entitled "Scanner Assembly" filed Feb. 21, 1992, which is herein incorporated by reference.

Figure 4A:
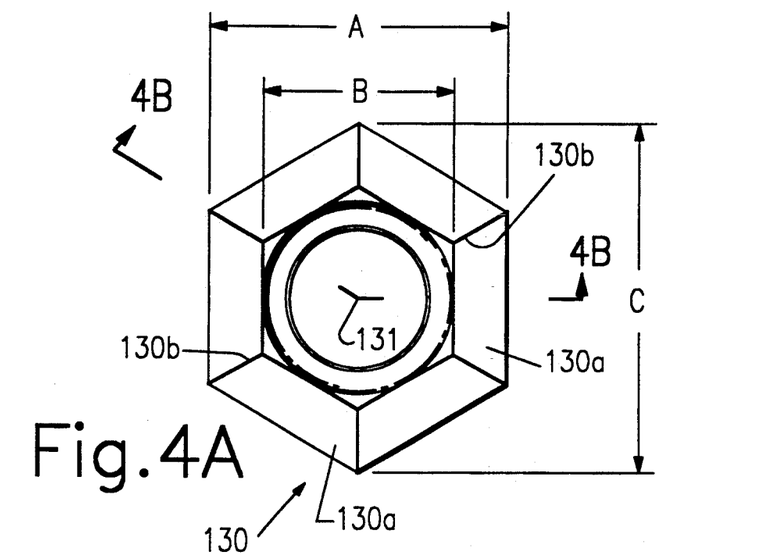
FIG. 4A is a plan view of the polygon mirror of FIG. 2 taken along line 4A—4A.
Figure 4B:
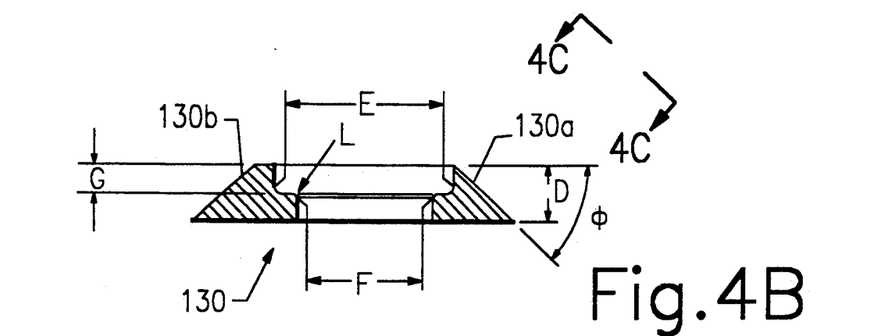
FIG. 4B is a cross sectional view of FIG. 4A taken along line 4B—4B.
Figure 4C:
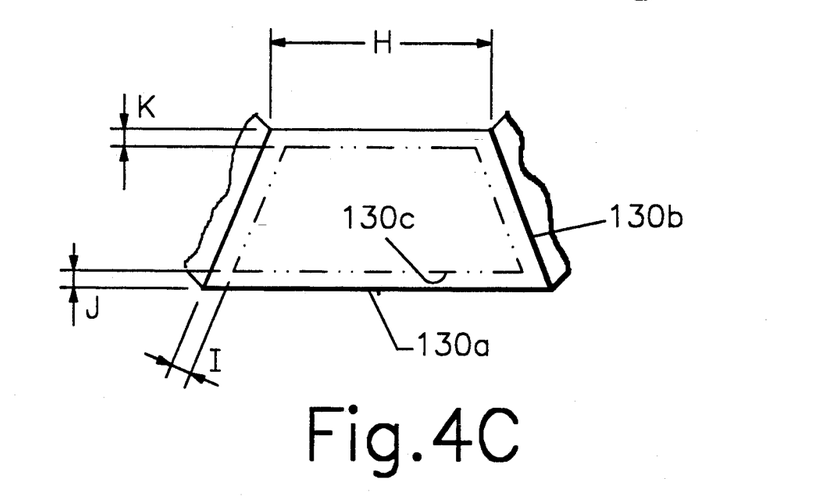
FIG. 4C is a plan view of a facet of the polygon mirror of FIG. 4B taken along line 4C—4C.

FIGS. 4A, 4B, and 4C illustrate details of a preferred optical polygon 130. The polygon 130 has six facets 130a, the polygon preferably being formed out of a single piece. The polygon is preferably made out of polycarbonate, but could be constructed out of acrylic or other optical materials including other plastics, metals or glass by one skilled in the art. The outer surface of each facet 130a may be advantageously coated with a suitable high reflective coating, the coating chosen would depend upon the optical material of the polygon 130. For example, a polycarbonate or acrylic facet may have a metallic coating such as gold (the preferred coating) or aluminum, while a metal or glass facet may be preferably coated with a single or multi-layered dielectric such as silicon dioxide ($SiO_2$) or titanium dioxide. As shown, each of the mirror facets 130a are generally trapezoidal in shape with adjacent facets joined along interfaces 130b. Each facet 130a comprises a central reflective surface 130c which is also generally trapezoidal in shape. The planar surface of the facets 130a are disposed at a 45° angle (from a plane perpendicular to the rotational axis 131 of the polygon 130) so that as shown in FIG. 3, the optical beam 115 from the fold mirror 125 is reflected along a desired path through the diffractive optical module 50 and toward the target.

The diffractive optical elements 50a and 50b are preferably holograms or Holographic Optical Elements (HOE's), diffractive optical elements created by holographic recording. Alternately, the diffractive elements comprise diffractive gratings which may be manufactured holographically (which is the preferred method), mechanically (such as by scribing or embossing), electron beam machining, electron ion milling or by other suitable method. The hologram material may be of any suitable type including photoresist, dichromatic gelatin, or photographic film.

In a preferred embodiment for a handheld laser diode scanner, which will be referred to as a standard long range scanner having a focused wavefront with a focal point located about 10" to 15" (25-38 cm) beyond the diffractive optical module 50, preferred construction dimensions referenced in the figures with identifying labels A-L and $\phi$ of FIGS. 4A, 4B and 4C may have the following values:

| A | 1.036 in. (2.631 cm) | F | 0.480 in. (1.219 cm) |
|---|---|---|---|
| B | 0.6560 in. (1.666 cm) | G | 0.099 in. (0.251 cm) |
| C | 1.196 in. (3.038 cm) | H | 0.378 in. (0.960 cm) |
| D | 0.190 in. (0.483 cm) | I | 0.045 in. (0.114 cm) |
| E | 0.620 in. (1.575 cm) | J, K | 0.025 in. (.0635 cm) |
| L | 0.010 in. (0.025 cm) × 45° chamfer | | |
| $\phi$ | 45°. | | |

Figure 5A:
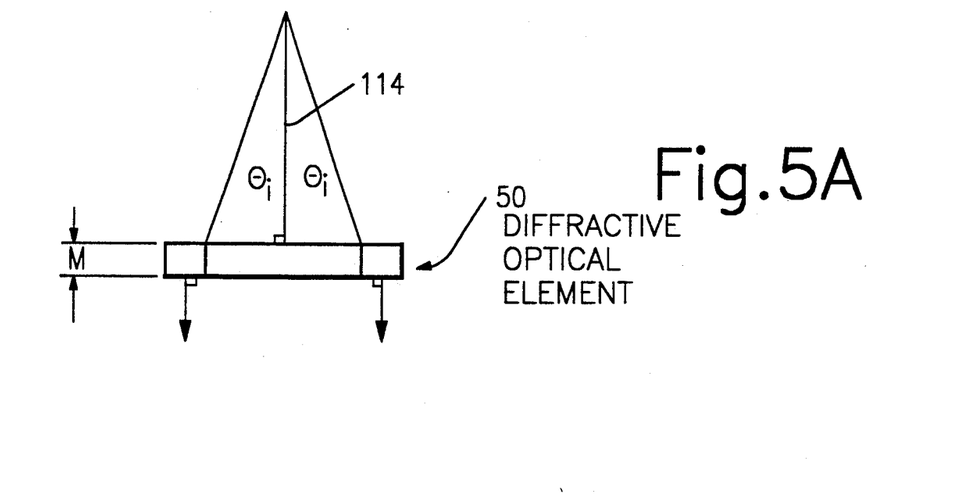
FIG. 5A is a top plan view of the grating of FIG. 3
Figure 5B:
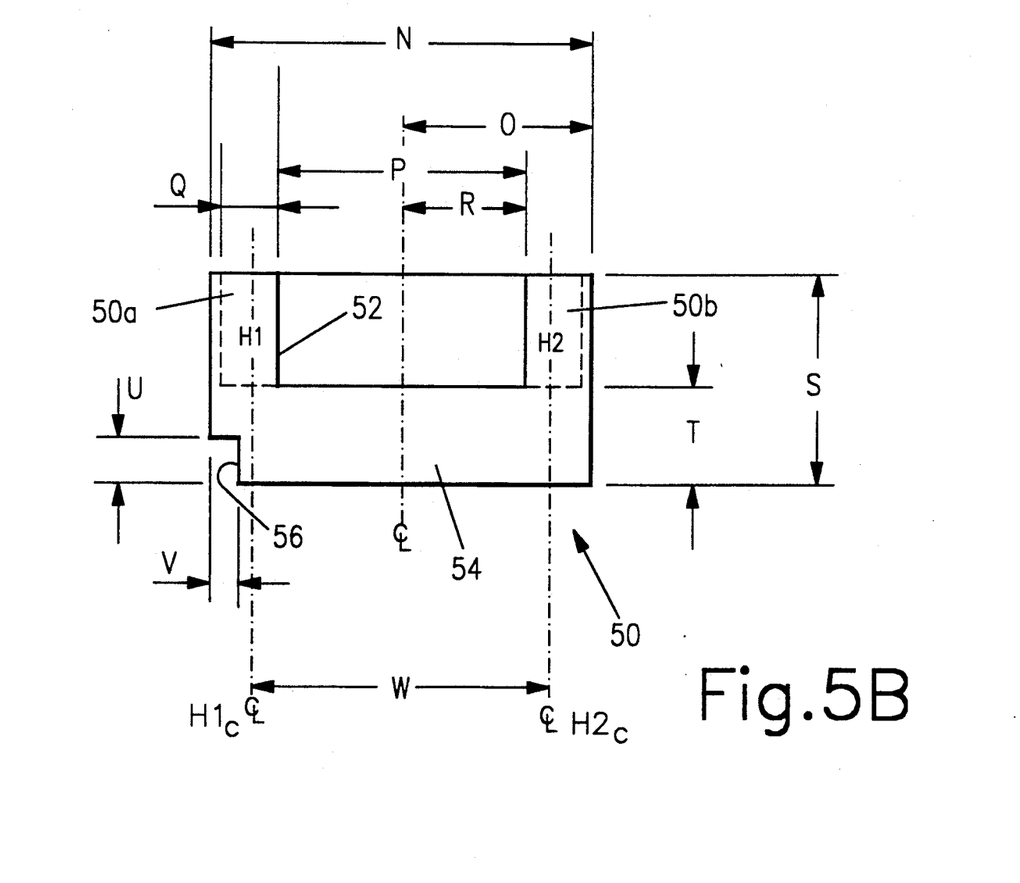
FIG. 5B is a front elevation view of the grating of FIG. 5A.

As described, the diffractive optical elements 50a and 50b are designed to reorient the portion of the scanning beam passing therethrough into columns or spots of light traveling generally parallel to the optical axis 114 toward the target. Details of a preferred design for module 50 is illustrated in FIGS. 5A and 5B. The module 50 is generally U-shaped with a base portion 54 which supports the first and second diffractive optical element 50a and 50b on each leg. A notch 56 is provided in a corner of the base portion 54 to assist in aligning the module 50 during installation.

The elements 50a and 50b are preferably HOE's holographically recorded to diffract incoming and converging light impinging thereon and redirect the light parallel to the optical axis to form the desired aiming spot at the expected distance. Between the elements 50a and 50b (also identified in FIG. 5B as elements H1 and H2 respectively) is an aperture or window 52 through which the scanning beam 115 may pass unimpeded. The incoming wavefront scans in the scan plane over a range $\Theta_i$, the angle of incidence on each side of the optical axis 114. The diffractive optical elements, 50a and 50b are oriented along centerlines H1$_c$ and H2$_c$ respectively.

The precise design for the module 50 will depend upon the particular application for the scanner and numerous related parameters. It is submitted that, given the disclosure herein, one skilled in the art could construct a suitable module 50. To assist in the construction of such a module by way of example, the following information is provided on the construction of a preferred design.

In preferred construction for a diffractive optical module 50 to be used with the polygon mirror of FIG. 4A, the preferred construction dimensions referenced in the figures with identifying labels M-W of FIGS. 5A and 5B may have the following values:

| M | 0.080 in. (0.200 cm) | S | 0.390 in. (0.991 cm) |
|---|---|---|---|
| N | 0.795 in. (2.019 cm) | T | 0.140 in. (0.357 cm) |
| O | 0.398 in. (1.011 cm) | U | 0.070 in. (0.178 cm) |
| P | 0.440 in. (1.118 cm) | V | 0.050 in. (0.127 cm) |
| Q | 0.090 in. (0.227 cm) | W | 0.49 in. (1.24 cm) |
| R | 0.220 in. (0.559 cm) | | |

The HOE is secured to a 0.795 in.×0.390 in. (2.019 cm×0.991 cm) polycarbonate substrate having a thickness of 0.080 in. (2 mm). In the preferred scanner design described, the angle of incidence $\Theta_i$ for the incoming wavefront will range from 22° to 30°. The incoming wavefront has a wavelength of 675 nm+5 nm−10 nm emitted from a laser diode. The incoming wavefront diameter is approximately 0.8 mm at the $1/e^2$ power points with the energy distribution within that wavefront being nominally Gaussian. The desired angle of refraction of the HOE grating is 0°+/−0.5° relative to the normal to the grating for the entire range of angles of incidence of the incoming wavefront. The HOE grating may "collimate" the beam incident upon the grating, but it may be acceptable to pass the beam on so that it will continue to focus (i.e. converge) as if the grating had not been present. Any other "shaping" of the output wavefront required should be able to be handled by the supplier of the hologram material. The optical diffraction efficiency is preferably at least 50%, however it is anticipated that efficiencies of these HOE's may reach 80% or higher.

Figure 6A:
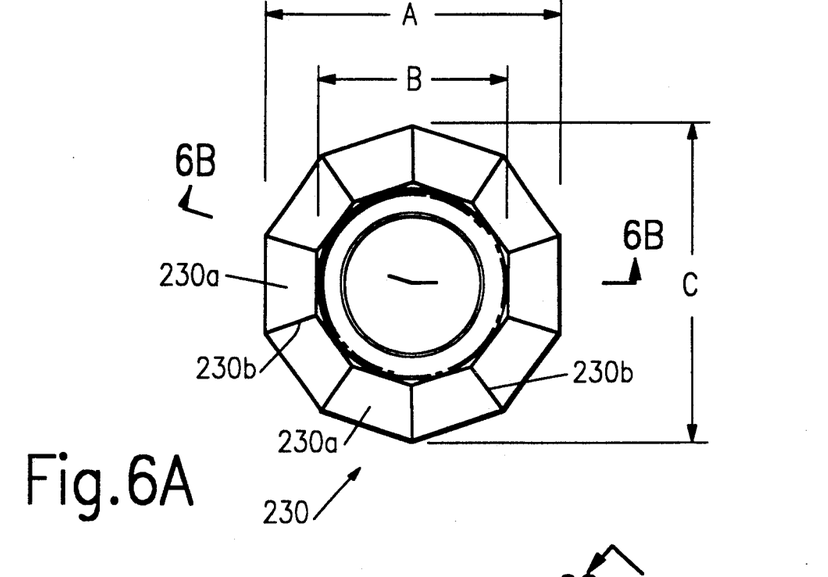
FIG. 6A is a plan view of a alternate polygon mirror.
Figure 6B:
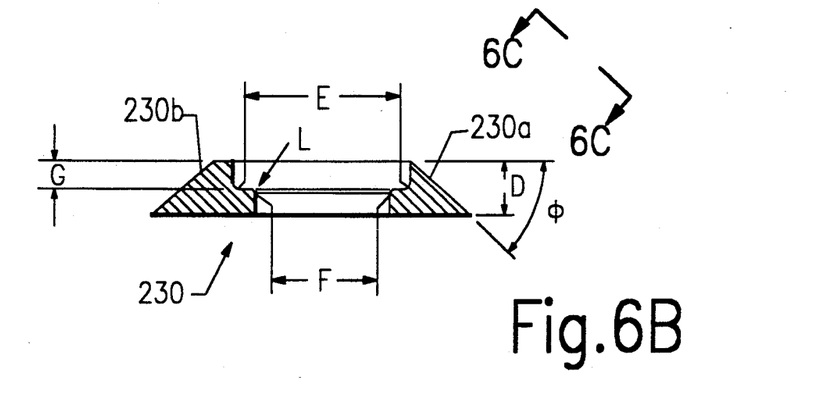
FIG. 6B is a cross sectional view of FIG. 6A taken along line 6B—6B.
Figure 6C:
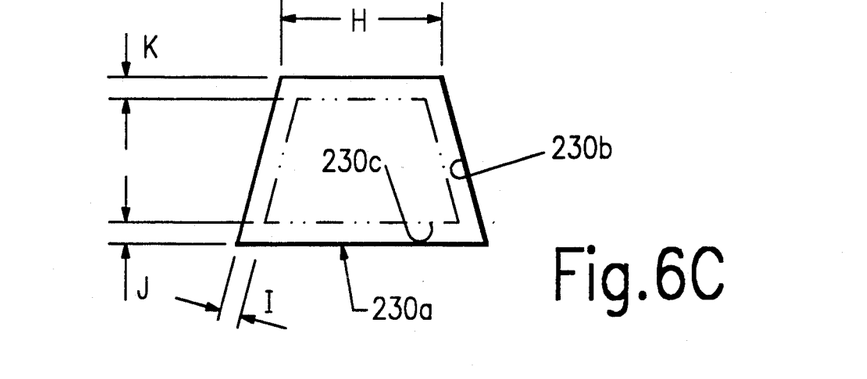
FIG. 6C is a plan view of a facet of the polygon mirror of FIG. 6B taken along line 6C—6C.

In a alternate embodiment for a long range handheld laser diode scanner, the scanner having a focused wavefront with a focal point located about 31" (80 cm) beyond the module 50, preferred construction dimensions referenced in the figures with identifying labels A-L of FIGS. 6A, 6B and 6C may have the following values:

| A | 1.060 in. (2.692 cm) | F | 0.460 in. (1.168 cm) |
|---|---|---|---|
| B | 0.680 in. (1.727 cm) | G | 0.099 in. (0.251 cm) |
| C | 1.115 in. (2.832 cm) | H | 0.221 in. (0.561 cm) |
| D | 0.160 in. (0.406 cm) | I | 0.025 in. (.0635 cm) |
| E | 0.620 in. (1.575 cm) | J, K | 0.025 in. (.0635 cm) |
| L | 0.010 in. (0.025 cm) × 45° chamfer | | |

| $\phi$ | 45°. |
|---|---|

Figure 7A:
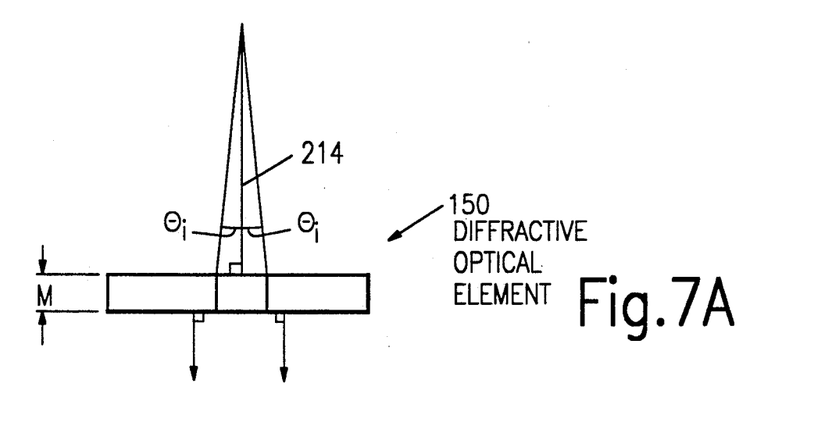
FIG. 7A is a top plan view of alternate grating.
Figure 7B:
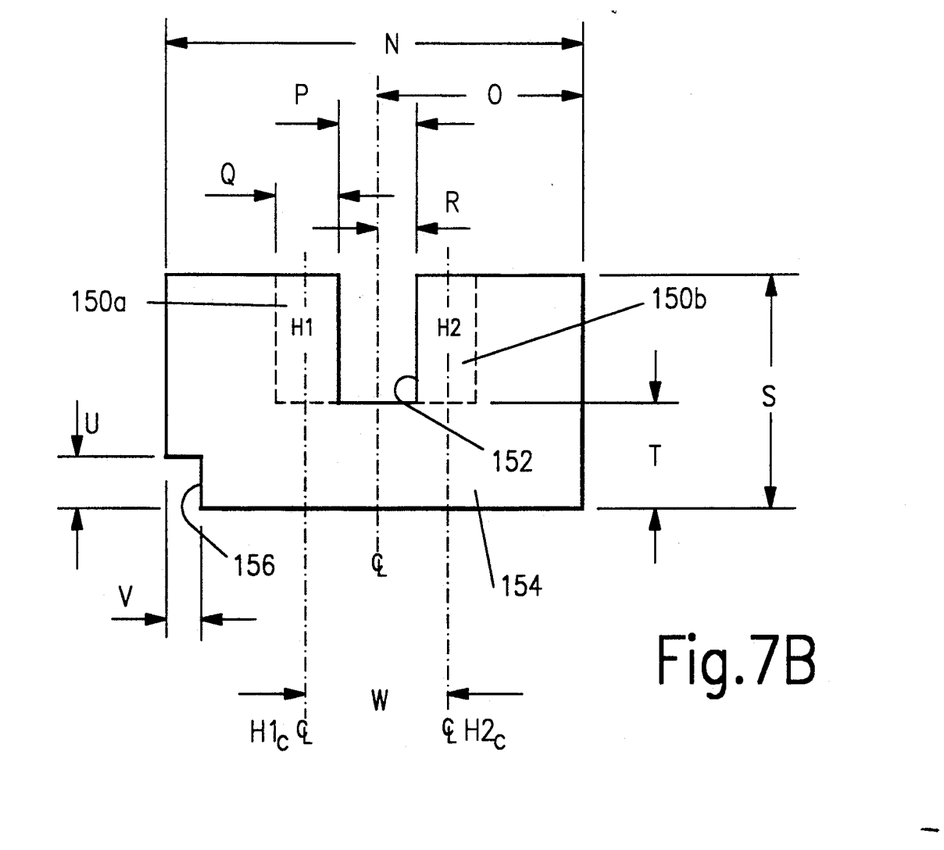
FIG. 7B is a front elevation view of the grating of FIG. 7A.

In the preferred construction for a grating 150 to be used with the alternate polygon mirror of FIG. 6A, preferred construction dimensions referenced in the figures with identifying labels M-W of FIGS. 7A and 7B may have the following values:

| M | 0.080 in. (0.203 cm) | S | 0.390 in. (0.991 cm) |
|---|---|---|---|
| N | 0.795 in. (2.019 cm) | T | 0.140 in. (0.357 cm) |
| O | 0.398 in. (1.011 cm) | U | 0.070 in. (0.178 cm) |
| P | 0.120 in. (0.305 cm) | V | 0.050 in. (0.127 cm) |
| Q | 0.090 in. (0.227 cm) | W | 0.209 in. (0.531 cm) |
| R | 0.060 in. (0.152 cm) | | |

In this embodiment, the HOE is secured to a 0.795 in.×0.390 in. (2.019 cm×0.991 cm) polycarbonate substrate having a thickness of 0.080 in. (2 mm). In the preferred scanner design described, the angle of incidence $\Theta_i$ for the incoming wavefront will range from 7° to 18°. The incoming wavefront has a wavelength of 675 nm+5 nm−10 nm emitted from a laser diode. The incoming wavefront diameter is approximately 0.8 mm at the $1/e^2$ power points with the energy distribution within that wavefront being nominally Gaussian. The desired angle of refraction of the HOE grating is 0°+/−0.5° relative to the normal to the grating for the entire range of angles of incidence of the incoming wavefront.

Thus, a scanning system and method for reading data have been shown and described. It is intended the aiming systems disclosed may be combined with any suitable collecting configuration or outgoing light configurations. Though certain examples and advantages have been disclosed, further advantages and modifications may become obvious to one skilled in the art from the disclosures herein. The invention therefore is not to be limited except in the spirit of the claims that follow.

What is claimed is:

1. An aiming system for an optical data reading device, comprising:
   a light source generating an optical beam along an outgoing optical path toward an object to be scanned;
   a detector for detecting light reflected off the object;
   a scan mirror in the outgoing optical path directing light toward the object along a scan plane; and
   a diffractive optical module positioned in the outgoing optical path adjacent the scan mirror, the diffractive optical module comprising:
   a pair of diffractive optical elements separated by an aperture, the diffractive optical elements positioned on either side of the aperture along the scan plane, each diffractive optical element descanning the portion of the optical beam passing therethrough to form an aiming light beam.

2. An aiming system according to claim 1 wherein the diffractive optical elements are selected from the group consisting of holograms, holographic optical elements, diffractive gratings.

3. An aiming system according to claim 1 wherein the diffractive optical elements are constructed by one of the methods selected from the group consisting of: holographically, mechanically, scribing, embossing, electron beam machining, electron ion milling.

4. An aiming system according to claim 1 wherein the diffractive optical elements comprise hologram material selected from the group consisting of photo resist, dichromatic gelatin and photographic film.

5. An aiming system according to claim 1 wherein the diffractive optical module comprises
a generally U-shaped structure having two legs and a base portion, a first diffractive optical element supported on one leg and a second diffractive optical element supported on the other leg.

6. An aiming system according to claim 1 wherein the aperture between the diffractive optical elements comprises an air gap.

7. An aiming system according to claim 1 wherein the diffractive optical grating has an optical efficiency of at least 50%.

8. A method of aiming a scanning system for optically reading data on a target object, comprising the steps of:
(a) generating an optical beam along an outgoing optical path;
(b) creating a scanning optical beam along a scan plane; and
(c) aiming the scanning optical beam by the steps of:
(i) passing only a portion of the scanning optical beam through at least one diffractive optical element positioned along the scan plane, (ii) de-scanning the portion of the scanning optical beam passing therethrough to form an aiming light beam travelling generally parallel to the outgoing optical path, and (iii) forming an aiming spot on the target object with the aiming light beam; and
(d) detecting light reflected or scattered off the target object.

9. A method of aiming according to claim 8 wherein the optical beam is scanned over the scan angle in a single scan plane.

10. A method of aiming according to claim 8 wherein the portion of the optical beam is de-scanned at an outer fringe of the scan angle.

11. A method of aiming according to claim 8 wherein the portion of the optical beam is de-scanned at outer fringes of the scan angle.

12. A method of aiming according to claim 8 wherein the portion of the optical beam is de-scanned by passing outer fringes of the scan angle of the scanned optical beam through diffractive optical elements.

13. A method of aiming according to claim 12 further comprising the step of passing the remaining portion of the optical beam through an aperture between the diffractive optical elements.

14. A method for data reading comprising the steps of:
(a) generating an optical beam along an outgoing optical path toward an object to be read;
(b) scanning the optical beam over a scan angle;
(c) de-scanning a first portion of the scanning optical beam to form a first aiming beam;
(d) using the first aiming beam as a guide to direct the scanning optical beam on the object.

15. A method for data reading according to claim 14 wherein the first portion of the scanning beam is located on one side of the scan angle.

16. A method for data reading according to claim 15 further comprising the steps of de-scanning a second portion of the scanning optical beam on a side of the scan angle opposite from the first portion of the scanning optical beam to form a second aiming beam.

17. A method for data reading according to claim 14 further comprising orienting the scanning optical beam by
locating the first portion of the scanning beam on one side of the scan angle,
forming a second aiming beam by de-scanning a second portion of scanning optical beam on a side of the scan angle opposite to the first portion of the scanning optical beam,
using the first and second aiming beams as guides to orient the scanning optical beam across the object.

18. A method for data reading according to claim 14 wherein the step of de-scanning comprises pressing the first portion of the scanning optical beam through a first diffractive optical element.

19. A method for data reading according to claim 14 wherein the step of de-scanning comprises passing the scanning optical beam through a diffractive optical module, the diffractive optical module having first and second diffractive optical elements positioned on opposite sides of a window, each diffractive optical element de-scanning the portion of the optical beam passing therethrough to form an aiming light beam.

20. A method for data reading according to claim 19 wherein the diffractive optical elements are selected from the group consisting of holograms, holographic optical elements, diffractive gratings.

21. A method for data reading according to claim 19 wherein the aiming beams travel in a path generally parallel to an optical axis of the scanning optical beam.

* * * * *